US008750966B2

(12) United States Patent
Phillips et al.

(10) Patent No.: US 8,750,966 B2
(45) Date of Patent: *Jun. 10, 2014

(54) METHOD FOR MARKING A TISSUE SAMPLE

(71) Applicants: Michael J. Phillips, Oconomowoc, WI (US); Janet L. F. Phillips, Oconomowoc, WI (US)

(72) Inventors: Michael J. Phillips, Oconomowoc, WI (US); Janet L. F. Phillips, Oconomowoc, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 13/647,892

(22) Filed: Oct. 9, 2012

(65) Prior Publication Data
US 2013/0040041 A1 Feb. 14, 2013

Related U.S. Application Data

(63) Continuation of application No. 13/205,195, filed on Aug. 8, 2011, now Pat. No. 8,594,768, which is a continuation-in-part of application No. 11/749,552, filed on May 16, 2007, now Pat. No. 8,301,227, application No. 13/647,892, which is a continuation-in-part of application No. 11/873,249, filed on Oct. 16, 2007, now abandoned, which is a continuation-in-part of application No. 10/978,948, filed on Nov. 1, 2004, now abandoned.

(60) Provisional application No. 60/800,714, filed on May 16, 2006.

(51) Int. Cl.
*A61B 17/22* (2006.01)
(52) U.S. Cl.
USPC .......................................... 600/424; 606/151
(58) Field of Classification Search
USPC ................... 600/424, 426; 128/898; 606/151
See application file for complete search history.

(56) References Cited

U.S. PATENT DOCUMENTS 2,138,241 A 11/1938 Koch et al.
2,297,990 A 10/1942 Schmitt et al.
(Continued)

FOREIGN PATENT DOCUMENTS

DE 3445085 2/1987
DE 10220238 A1 1/2004
JP 03051200 A 3/1991

OTHER PUBLICATIONS

About Rubber Stamps.Com; Rubber Stamps and rubber stamp accessories from Inkadinkado; Colorbox Ink Pads—3 colors; website: www.aboutrubberstamps.com/colorbox3colors.html; Sep. 27, 2004, 1 page.

*Primary Examiner* — Parikha Mehta
(74) *Attorney, Agent, or Firm* — Barbara A. Wrigley; Oppenheimer Wolff & Donnelly LLP

(57) ABSTRACT

A tissue marking system for use in marking a tissue sample comprises an ink-based applicator device and at least one tissue marking clip. The ink-based applicator device includes a container, a first number of ink reservoirs at least partially defined by the container, wherein each reservoir contains ink of a different color, a second number of applicators, wherein each applicator is configured to absorb a quantity of ink for application to the tissue sample, and a cover coupled to and cooperating with the container to fully enclose each of the first number of ink reservoirs. The at least one tissue marking clip includes an actuator portion movable between an actuated position and a non-actuated position, and a jaw portion coupled to the actuator portion and movable between an open position and a closed position in response to movement of the actuator portion between the actuated and non-actuated positions.

11 Claims, 11 Drawing Sheets

(56) References Cited

U.S. PATENT DOCUMENTS

| | | |
|---|---|---|
| 2,643,765 A | 6/1953 | Bradshaw |
| 2,738,606 A | 3/1956 | Klein |
| 2,932,906 A | 4/1960 | Chamberlain |
| 3,352,280 A | 11/1967 | Hughes at al. |
| 3,635,808 A | 1/1972 | Elevitch |
| 4,025,393 A | 5/1977 | Hirschfeld |
| 4,034,700 A | 7/1977 | Bassett et al. |
| 4,510,119 A | 4/1985 | Hevey |
| 4,584,042 A | 4/1986 | Wandroik |
| 4,681,471 A | 7/1987 | Hayduchok et al. |
| 4,739,906 A | 4/1988 | LoTurco |
| 5,092,184 A | 3/1992 | Goodell et al. |
| 5,098,661 A | 3/1992 | Froehlich et al. |
| 5,474,569 A | 12/1995 | Zinreich et al. |
| 5,667,526 A | 9/1997 | Levin |
| 5,670,118 A | 9/1997 | Sponholtz |
| 5,743,899 A | 4/1998 | Zinreich |
| 5,865,305 A | 2/1999 | Yasoshima |
| 5,895,762 A | 4/1999 | Greenfield et al. |
| 5,902,310 A | 5/1999 | Foerster et al. |
| 5,927,009 A | 7/1999 | Vanwingerden |
| 5,955,352 A | 9/1999 | Inoue et al. |
| 5,958,341 A | 9/1999 | Chu |
| 6,247,211 B1 | 6/2001 | Bell |
| 6,254,826 B1 | 7/2001 | Acosta et al. |
| 6,286,682 B1 | 9/2001 | d'Arbelles |
| 6,321,487 B1 | 11/2001 | Sardanelli et al. |
| 6,372,313 B1 | 4/2002 | D'Alessio et al. |
| 6,372,895 B1 | 4/2002 | Bentsen et al. |
| 6,415,714 B2 | 7/2002 | Winston |
| 6,464,506 B1 | 10/2002 | Welles |
| 6,569,676 B1 | 5/2003 | Tripp et al. |
| 6,703,247 B1 | 3/2004 | Chu |
| 6,723,290 B1 | 4/2004 | Wardlaw |
| 6,725,802 B1 | 4/2004 | Carrington et al. |
| 6,740,068 B1 | 5/2004 | Arrufoo et al. |
| 6,743,228 B2 | 6/2004 | Lee et al. |
| 6,780,179 B2 | 8/2004 | Lee et al. |
| 6,826,257 B2 | 11/2004 | Sayre et al. |
| 6,945,017 B1 | 9/2005 | Bonney et al. |
| 7,569,065 B2 | 8/2009 | Chesbrough et al. |
| 7,657,300 B2 | 2/2010 | Hunter et al. |
| 7,870,951 B1 | 1/2011 | Orsi |
| 2001/0025579 A1 | 10/2001 | Winston |
| 2003/0204137 A1 | 10/2003 | Chesbrough et al. |
| 2003/0220640 A1 | 11/2003 | Lee et al. |
| 2005/0234322 A1 | 10/2005 | Lober |
| 2006/0229529 A1 | 10/2006 | Wright |

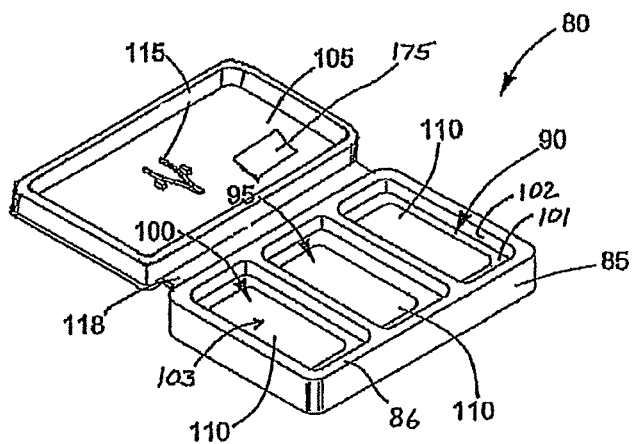
FIG. 5
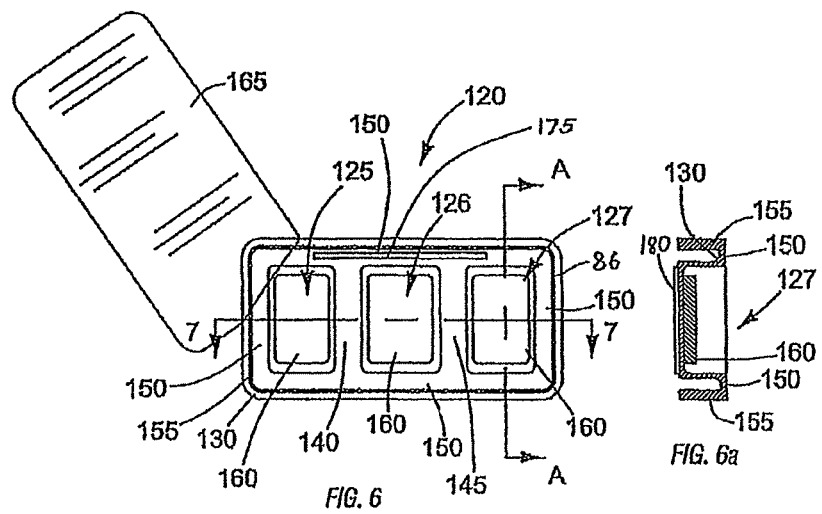
FIG. 6
FIG. 6a

METHOD FOR MARKING A TISSUE SAMPLE

CROSS-REFERENCE TO RELATED APPLICATIONS

This application is a continuation of U.S. application Ser. No. 13/205,195, filed on Aug. 8, 2011, now U.S. Pat. No. 8,594,768 B2, issued on Nov. 26, 2013, which is a continuation-in-part of U.S. application Ser. No. 11/749,552, filed May 16, 2007, now U.S. Pat. No. 8,301,227, issued on Oct. 30, 2012, which claims the benefit of U.S. Provisional Ser. No. 60/800,714, filed May 16, 2006, the entireties of which are hereby incorporated by reference. This application is also a continuation-in-part of U.S. application Ser. No. 11/873,249 (abandoned), filed Oct. 16, 2007, which is a continuation-in-part and claims the benefit of U.S. application Ser. No. 10/978,948 (abandoned), filed Nov. 1, 2004, the entireties of which are hereby incorporated by reference.

BACKGROUND OF THE INVENTION

The present invention relates to a tissue marking system. More particularly, the present invention relates to a tissue marking system that identifies tissue orientation during both radiographic and visual examination.

During surgery, it is often necessary to remove a sample of tissue and closely examine that tissue sample (e.g., radiographic examination) while knowing its original orientation within the patient. For example, cancerous tumors are often removed from the patient and then examined to verify that a sufficient margin of tissue surrounding the tumor has been removed. To determine this, the tissue sample is examined and the margins on each surface are identified. If a margin is insufficient, it is important for the surgeon to know the orientation of the sample to allow for the removal of additional tissue in the proper area.

Presently, different color sutures, different length sutures, or different quantities of sutures are inserted into the tissue sample to identify the orientation of the tissue. However, this is time consuming and the sutures can be accidentally removed making identification of the tissue orientation difficult. Furthermore, sutures are not visible in radiographic (X-ray) images. As such, the tissue sample must be marked in a second way to provide for orientation in any X-ray images that may be taken.

SUMMARY OF THE INVENTION

The present invention solves the foregoing problems by providing a tissue marking system for use in marking a tissue sample that comprises an ink-based applicator device and at least one tissue marking clip. The ink-based applicator device includes a container, a first number of ink reservoirs at least partially defined by the container, wherein each reservoir contains ink of a different color, a second number of applicators, wherein each applicator is configured to absorb a quantity of ink for application to the tissue sample, and a cover coupled to and cooperating with the container to fully enclose each of the first number of ink reservoirs. The at least one tissue marking clip includes an actuator portion movable between an actuated position and a non-actuated position, and a jaw portion coupled to the actuator portion and movable between an open position and a closed position in response to movement of the actuator portion between the actuated and non-actuated positions. The jaw portion includes a first tooth and a second tooth configured to engage the tissue sample when the jaw portion moves from the open position to the closed position.

In another aspect of the invention, a tissue marking method for marking a tissue sample is provided that comprises the steps of providing a container including a first ink reservoir containing a first color ink, a second ink reservoir containing a second color ink, and a third ink reservoir containing a third color ink, applying the first color ink to a first surface of the tissue sample, applying the second color ink to a second surface of the tissue sample, applying the third color ink to a third surface of the tissue sample, providing first, second, and third tissue marking clips, wherein each of the tissue marking clips includes an actuator portion movable between a non-actuated position and an actuated position and a jaw portion coupled to the actuator portion and movable between an open position and a closed position in response to movement of the actuator portion, clipping the first tissue marking clip on the first surface of the tissue sample, clipping the second tissue marking clip on the second surface of the tissue sample, and clipping the third tissue marking clip on the third surface of the tissue sample.

Other aspects of the invention will become apparent by consideration of the detailed description and accompanying drawings.

BRIEF DESCRIPTION OF THE DRAWINGS

FIG. 5 is a perspective view of a tissue marking system;

FIG. 6 is a top view of another tissue marking system;

FIG. 6a is a sectional view of the tissue marking system of FIG. 6 taken along line A-A of FIG. 6;

DETAILED DESCRIPTION OF THE INVENTION

Figure 1:
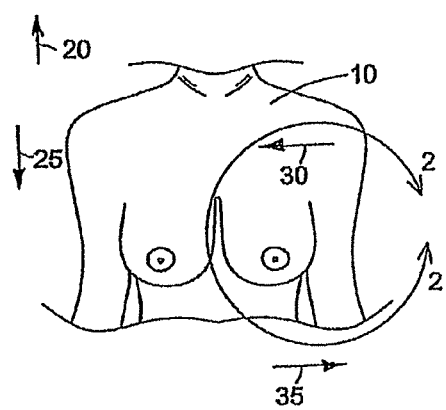
FIG. 1 is a top view of a patient including a tissue sample to be removed from the patient.
Figure 2:
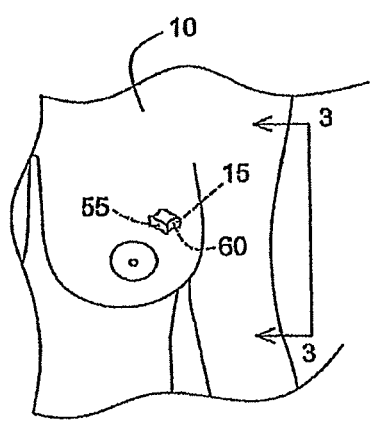
FIG. 2 is an enlarged top view of a portion of the patient and tissue sample of FIG. 1.
Figure 3:
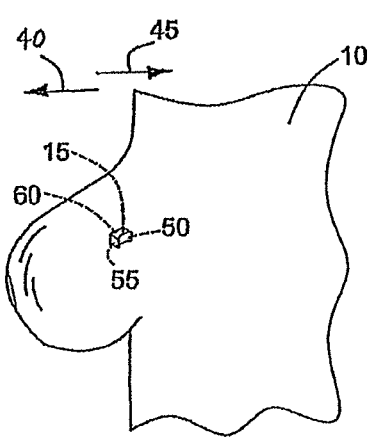
FIG. 3 is a side view of the portion of the patient and tissue sample of FIG. 1.

With reference to FIGS. 1-3, a patient 10 and a tissue sample 15 are illustrated to show the tissue sample's orientation in the patient 10. Before proceeding, it should be noted that the present invention will be described as it relates to a tissue sample 15 removed from a breast. However, one of ordinary skill in the art will realize that the invention is applicable to many other tissue samples in which orientation is important. For example, basal cell carcinoma also requires that a tissue sample be removed, and that its orientation be identified to verify that sufficient margin has been removed. As such, the invention should not be limited only to the uses described herein as it is well suited for use with any tissue that required orientation for pathology and/or radiology. These tissues include but are not limited to samples of breast, bone, thyroid, lymph nodes, brain, sarcomas, kidney, bowel, spleen, soft tissue masses, melanoma, squamous cell skin cancer, basal cell cancer, liver tumors, and the like.

FIG. 1 shows a view looking down on the patient 10. For purposes of description, the direction 20 toward the patient's head will be identified as superior, while the opposite direction 25 is inferior. The direction 30 toward the patient's midline is defined as medial, while the opposite direction 35 is defined as lateral. With reference to FIG. 3, a side view of a portion of the patient is illustrated to further illustrate orientation. The direction 40 toward the patient's exterior is defined as superficial, while the opposite direction 45 is defined as deep.

Figure 4:
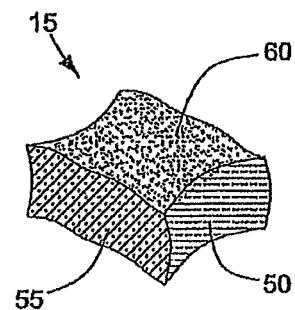
FIG. 4 is a perspective view of the tissue sample of FIG. 1 after being removed from the patient of FIG. 1.

FIGS. 2 and 3 illustrate the tissue sample 15 within the patient 10 prior to its removal, while FIG. 4 shows that same tissue sample 15 after removal. With the sample 15 still in the patient 10, the three surfaces 50, 55, 60 that will be marked can be seen. While any three planes or surfaces of the tissue sample 15 can be used to identify the orientation of the sample 15, it is preferred that at least three substantially orthogonal surfaces be identified, with some applications marking six surfaces. In FIGS. 2 and 3, the lateral surface 50, inferior surface 55, and superficial surface 60 of the tissue sample 15 are shaded differently for illustrative purposes. In FIG. 4, the same three surfaces 50, 55, 60 are shaded to indicate that they have been marked with a different color.

Before proceeding, it should be noted that the term "ink" as used herein is meant to encompass any coloring element that can be applied to a tissue sample 15, with dye, paint, and stains being a few examples. As such, the invention should not be limited to ink alone.

To mark the surfaces 50, 55, 60, three different color inks are employed. FIG. 5 illustrates a container 80 suited for use in marking the tissue sample 15. The container 80 includes a housing 85 that defines three substantially separated compartments 90, 95, 100 and a cover 105 pivotally attached to the housing 85. A perimeter 86 extends around the container 80 and encircles the three compartments 90, 95, 100. Each of the three different color inks is disposed within one of the three compartments 90, 95, 100. The cover 105 is movable between a covering position where it covers the three compartments 90, 95, 100 and cooperates with the housing 85 to completely separate the compartments 90, 95, 100, and an open position where the ink is accessible.

Each compartment 90, 95, 100 includes a bottom surface and a wall that surrounds the bottom surface. Opposite the bottom surface is an opening that allows for access to the ink during use.

In some constructions, each of the inks is simply disposed within one of the compartments 90, 95, 100. Generally, the ink in the compartments is in liquid form. In other constructions, an ink absorbent material 110, such as foam or felt, is disposed within each compartment 90, 95, 100 and is operable to absorb and hold the ink to inhibit spillage and mixing between the ink compartments 90, 95, 100.

Each quantity of ink is a different color than the remaining two quantities of ink. Thus, the first quantity of ink may be yellow, the second quantity of ink may be red, and the third quantity of ink may be black. Of course different colors (e.g., black, blue, green, red, yellow, orange, violet, and the like) could also be employed if desired. In addition, different colors may be employed depending on the particular tissue sample 15 to be removed. For example, breast tissue may be better examined if yellow, red, and blue inks are used, while basal cell samples may be better examined using red, blue, and black ink. Thus, the actual colors employed may be varied greatly.

Generally, the container 80 is a single use tool that is used during a single surgical procedure or a series of surgical procedures performed during the course of a single day. Thus, the container 80 and its contents are sterilized. While many different sterilization procedures are possible, it is believed that gamma ray sterilization is best suited to the task of sterilizing the container 80 and its contents with other sterilization processes also being possible. The container is subjected to a sufficient time and duration of gamma irradiation to render said container sufficiently sterile for introduction into a surgical operating room. In some constructions, a forceps 115 or tweezers is attached to the cover 105 and can be removed for use in grasping and marking the tissue sample 15. Thus, the tissue sample 15 can be marked using the enclosed forceps 115 and the forceps 115 and the container 80 can be discarded after use.

While many different manufacturing processes are possible it is preferred that the container 80, including the cover 105, be injection molded as a single component. In constructions that are molded as a single component, a living hinge 118 would generally be employed between the cover 105 and the housing 85. Of course, other manufacturing methods and other connections between the cover 105 and housing 85 could be employed if desired.

FIG. 6 illustrates another container 120 that supports three ink reservoirs 125, 126, 127 and is suited for use in marking the tissue sample 15. Like the container 80, the container 120 is a single use tool that is used during a surgical procedure or a series of surgical procedures throughout a day. For example, one container could be opened during a first surgical procedure and could be used throughout the day for a series of procedures before being discarded. In preferred constructions, the container 120 and its contents are sterilized before they are opened. The container 120 includes a formed portion 130 that defines the three ink reservoirs 125, 126, 127. The reservoirs 125, 126, 127 are slight depressions in the formed portion 130 that are sized to contain a quantity of ink. A first isolation space 140 is formed between the first reservoir 125 and the second reservoir 126 and a second isolation space 145 is formed between the second reservoir 126 and the third reservoir 127. The formed portion 130 also defines a perimeter 150 that surrounds the three reservoirs 125, 126, 127. In most constructions, the perimeter 150, the first isolation space 140, and the second isolation space 145 are all substantially disposed within a single plane and the reservoirs 125, 126, 127 extend below that plane.

In some constructions, a ridge 155 (shown in FIG. 6a) is formed around the perimeter 150 to increase the stiffness of the formed portion 130. The ridge 155 may have a semicircular, square, triangular, polygonal, or any other suitable cross-section. Generally, the ridge 155 extends downward below the perimeter to provide the additional stiffness. The ridge 155 also reduces the likelihood of tearing a surgical glove by reducing the number of sharp edges. The increased stiffness that results from the ridge 155 allows the container 120 to be used without being completely supported from beneath the reservoirs 125, 126, 127.

The ink, dye, or other marking substance is disposed within each of the reservoirs 125, 126, 127. As discussed with regard to FIG. 5, an ink absorbing material 160 such as felt or foam, can be placed within each of the reservoirs 125, 126, 127 to hold the ink and reduce the likelihood of spillage and mixing.

A cover 165 extends over the top of the open reservoirs 125, 126, 127 and sealably engages the perimeter 150, the first isolation space 140, and the second isolation space 145. The cover 165 inhibits spillage, mixing, drying, and contamination of the ink before and after sterilization. In most constructions, the cover 165 is a thin plastic film or a thin foil that is adhesively bonded, heat sealed, or otherwise attached to the formed portion 130. In adhesively bonded constructions, an adhesive is applied to the one or both of the cover 165 and the formed portion 130 in, or adjacent to, the perimeter 150, the first isolation space 140, and the second isolation space 145 such that when the cover 165 is positioned as desired, the cover 165 adhesively bonds to the formed portion 130. Once sealed by the cover 165, the container 120 and the ink can be sterilized, transported, and stored for future use.

It should be noted that the thin plastic cover 165 could be used with the construction of FIG. 5 in place of, or in conjunction with, the cover 105.

To manufacture the container 120, the formed portion 130 is first stamped or injection molded from a thermoplastic material. Of course other materials (e.g., metals, composites, and the like) and other manufacturing processes could be used if desired. The ink holding component 160 (e.g., felt, foam, etc.) is positioned within each of the reservoirs 125, 126, 127 if employed. The different color inks are then placed in the individual reservoirs 125, 126, 127. Adhesive is applied to one, or both, of the cover 165 and the formed portion 130 and the cover 165 is positioned on the formed portion 130 to complete the assembly of the container 120. The container 120 is then sterilized and packaged for use at a future date.

Figure 7:
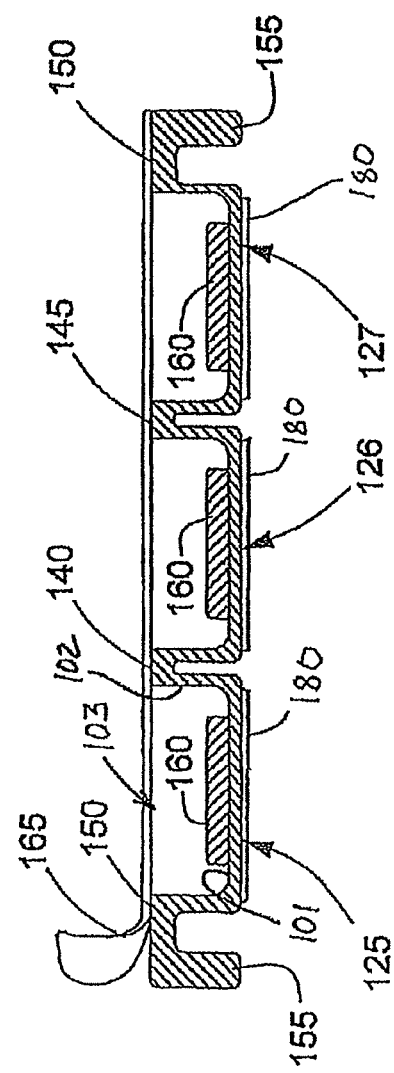
FIG. 7 is a sectional view of the tissue marking system of FIG. 6 taken along line 7-7 of FIG. 6.

FIG. 7 is a sectional view taken along the longitudinal axis of the container 120 of FIG. 6. As can be seen, the perimeter 150, the first isolation space 140 and the second isolation space 145 reside in a single plane that allows the cover to sealably engage the container and seal each reservoir from the other reservoirs. The ridge 155 extends downward to increase the stiffness of the container 120 and to eliminate a thin edge that would otherwise exist and would provide a sharp surface that could tear a surgical glove.

In use, the constructions of FIG. 5 and FIGS. 6, 6a, and 7 function similarly. The cover 105, 165 is first opened or removed to expose the ink. A first surface 50 of the tissue sample 15 is dipped into the first reservoir 90, 125, a second surface 55 of the tissue sample 15 is dipped into the second reservoir 95, 126, and a third surface 60 of the tissue sample 15 is dipped into the third reservoir 100, 127. In most constructions, quick-drying ink is used to further speed the process. Generally, quick-drying ink is ink that dries in less than about 15 minutes with inks that dry in less than 5 minutes being preferred. The ink has a degree of viscosity such that it does not run or drip on the wet tissue after it is applied. Once the three surfaces 50, 55, 60 are marked, the orientation of the tissue sample 15 is easily identified and someone other than the surgeon can examine the sample while accurately understanding the original orientation of the tissue within the patient's body.

In some constructions, a label 175 is provided with the container 120 as shown in FIGS. 5 and 6. The label 175 is pre-marked with the ink colors and a space. The nurse or surgeon can identify the surface marked with each color ink by identifying that surface in the space adjacent the correct color on the preprinted label. The label 175 is then pealed off and affixed to the tissue sample 15 or the container that contains the tissue sample 15. In still other constructions, preprinted labels include the colors and a preprinted surface identification, thereby eliminating the need to write the orientation on the label. In addition, some constructions include duplicate labels to allow for easy identification on a patients chart.

It should be noted that all of the constructions illustrated and discussed herein could also include a stick surface 180 (shown in FIGS. 6a and 7). The stick surface reduces the likelihood of the container slipping off of a surface when the container 80, 120 is positioned for use. As such, the stick surface 180 is generally positioned opposite a reservoir opening, as illustrated in FIGS. 6a and 7. Many substances (e.g., rubber, VELCRO, adhesives, and the like) can be used as a stick surface 180.

Figure 8:
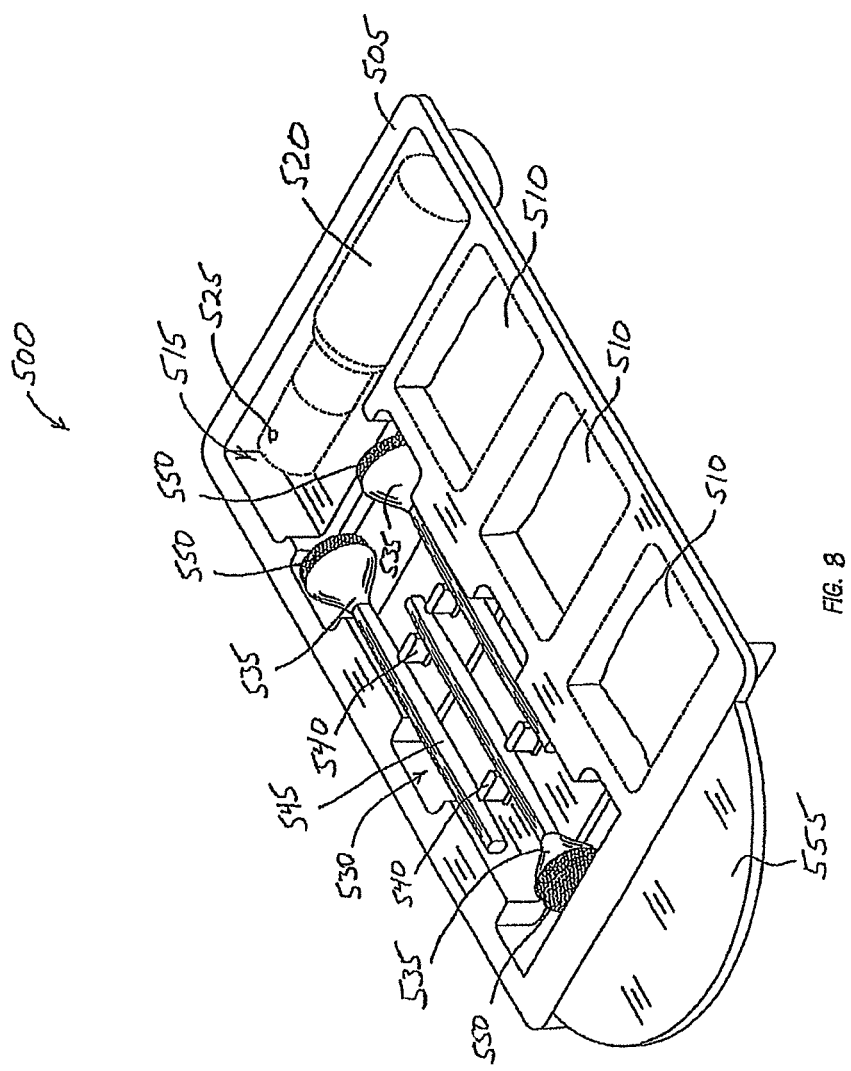
FIG. 8 is a perspective view of another construction of the tissue marking system.

FIG. 8 illustrates another construction of a single-use tissue marking system 500 that includes a container 505 preferably formed as a single unitary piece using a thermoplastic material. The container 505 defines three reservoirs 510 sized to contain a quantity of ink or die. The container 505 includes another compartment or space 515 sized to receive a container of fixative 520. The fixative 520 can be applied to the tissue sample before or after the ink or die is applied to improve the adhesion of the ink or die and inhibit running and drops. One fixative 520 suitable for use includes vinegar or a vinegar solution, with other fixatives 520 also being possible depending on the type of ink or die employed. In preferred constructions the fixative 520 is contained in a bottle with a spray nozzle 525. The spray nozzle 525 assures that a fine mist of fixative is sprayed onto the tissue rather than large droplets.

The container 505 defines an elongated space 530 that is sized to receive a plurality of applicators 535. In preferred constructions, the quantity of applicators 535 equals the quantity of ink reservoirs 505. As such, the illustrated construction includes three ink reservoirs 505 and three applicators 535. However, other constructions may include a different number of applicators 535 than reservoirs 505. For example, one construction could include six ink reservoirs 505 and three applicators 535. As one of ordinary skill will realize, many different quantities of applicators 535 and reservoirs 505 can be employed. For example, some constructions may include six ink reservoirs 505 and six applicators 535.

In the illustrated construction, the elongated space 530 includes a plurality of separator elements 540 that support and separate the applicators 535 within the space 530. The positioning within the space 530 allows a surgeon or other user to easily remove the applicators 535 with a gloved hand and with little risk of tearing or puncturing the glove.

Each applicator 535 includes a handle portion 545 and a sponge portion 550. In preferred constructions, the handle portion 545 is formed from a plastic material. The sponge portion 550 is sized to absorb and hold a desired quantity of ink, while facilitating the accurate placement of the ink on the tissue sample. By depressing the sponge 550 onto the tissue sample, the surgeon is able to release a desired quantity of ink without causing drips or runs that can blur or confuse the marking.

A removable cover member (not shown) similar to that illustrated in FIGS. 6, 6a, and 7 is employed to cover the container 505. The cover adhesively bonds to the container 505 and seals each ink reservoir 510 from the other ink reservoirs, the fixative space 515, and the elongated space 530 to inhibit leakage of the inks. In preferred constructions, a single one-piece cover is employed to expedite the opening of the ink reservoirs 510 and other spaces 515, 530.

As with the prior embodiments, the container 505 is a single-use device that is preferably sterilized prior to use. The user or surgeon grasps a handle 555 and removes the cover from the container 505 to completely expose each of the inks for use. Each applicator 535 is used with one of the inks to apply the ink to the tissue sample. The fixative 520 is applied before or after the ink is applied to assure that the ink remains fixed to the tissue sample. Once the tissue sample is properly marked, the container 505, cover, and applicators 535 can be discarded.

Figure 9:
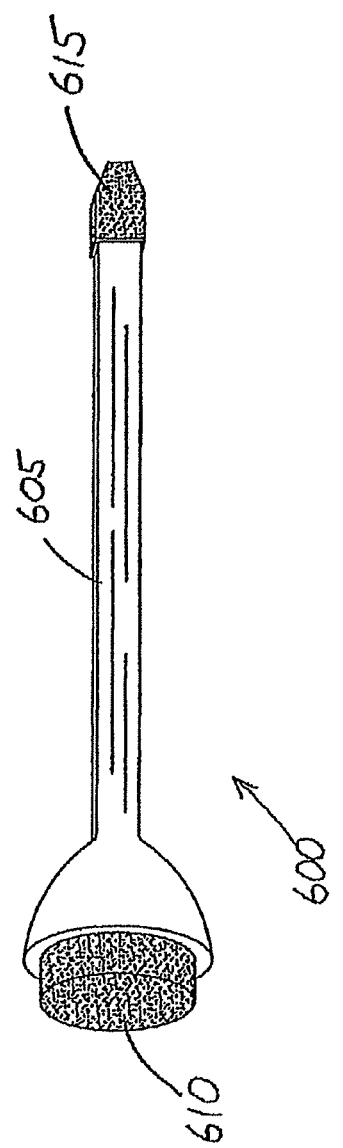
FIG. 9 is a perspective view of an applicator.

As noted, other constructions of the applicator are also possible. As illustrated in FIG. 9, one construction of an applicator 600 includes a handle portion 605, a first sponge portion 610, and a second sponge portion 615. The first sponge portion 610 is similar to the sponge portion 550. The second sponge portion 615 includes a sponge or other material that will hold a quantity of ink. However, the second sponge portion 615 includes a small edge that allows for the finer more accurate placement of ink should it be necessary.

Figure 10:
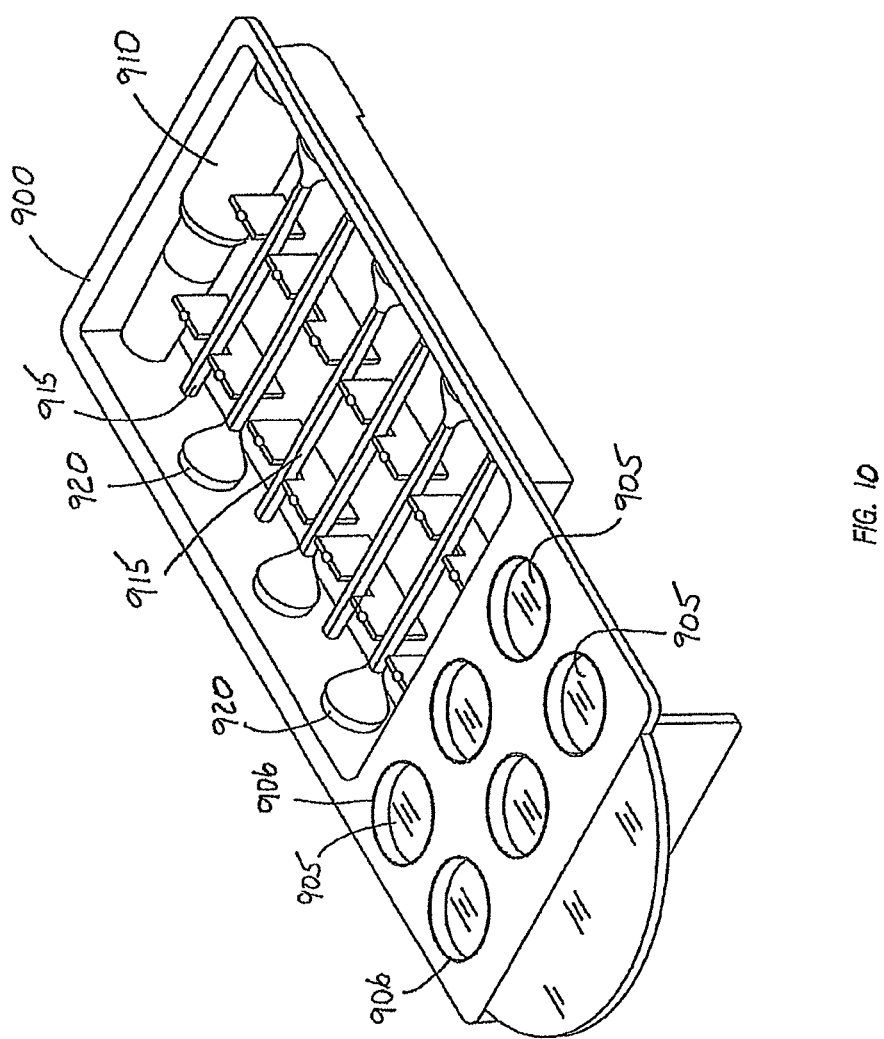
FIG. 10 is a perspective view of another construction of the tissue marking system.

As was also noted, other constructions may employ more reservoirs to hold more colors of ink and may include more applicators. For example, FIG. 10 illustrates a construction that includes a housing 900 that defines six reservoirs 905 that can be filled with six different colors of ink or dye as desired. In some cases, six different color inks are preferred to allow the surgeon to identify all six sides of the tissue sample. Alternatively, preferred colors can be used depending on the type of tissue or tumor.

Each reservoir 905 is surrounded by a ridge 906 that engages a cover (not shown) to assure that when the cover is in place, each reservoir 905 is sealed to inhibit leakage of ink from the reservoir 905.

In some constructions, each of the reservoirs 905 is labeled to aid the surgeon in properly marking the tissue sample. For example, one construction includes one of anterior, posterior, superior, inferior, medial, or lateral adjacent each of the reservoirs 905. Of course other labels could be employed if desired.

The construction of FIG. 10 also includes a bottle of fixative 910 and six applicators 915 rather than the three illustrated in FIG. 8. Each applicator 915 would typically be used with only one color ink to inhibit mixing of colors. While the illustrated applicators 915 include a single sponge end 920, other constructions could employ the applicator 600 illustrated in FIG. 9 if desired.

As with prior constructions, the housing 900 is covered with a single cover (not shown) that seals each of the reservoirs 905 and is removable to expose each of the six reservoirs 905, applicators 915, and fixative 910 for use. Once the cover is removed, the product is used for one or more surgical procedures and then is discarded. Thus, the construction of FIG. 10 is a single-use device.

Now that various ink marking systems in accordance with the invention have been described with reference to FIGS. 1-10, several exemplary embodiments of a tissue marking clip that may be used alone or in combination with an ink-based tissue marking system will now be set forth in detail. As will be appreciated by one of ordinary skill in the art, it is not possible to identify orientation of a tissue sample in a radiographic image using different color inks. Therefore, the use of a second marking means such as the marking clips is necessary when both radiographic and visual examination of a tissue sample is required.

Figure 11:
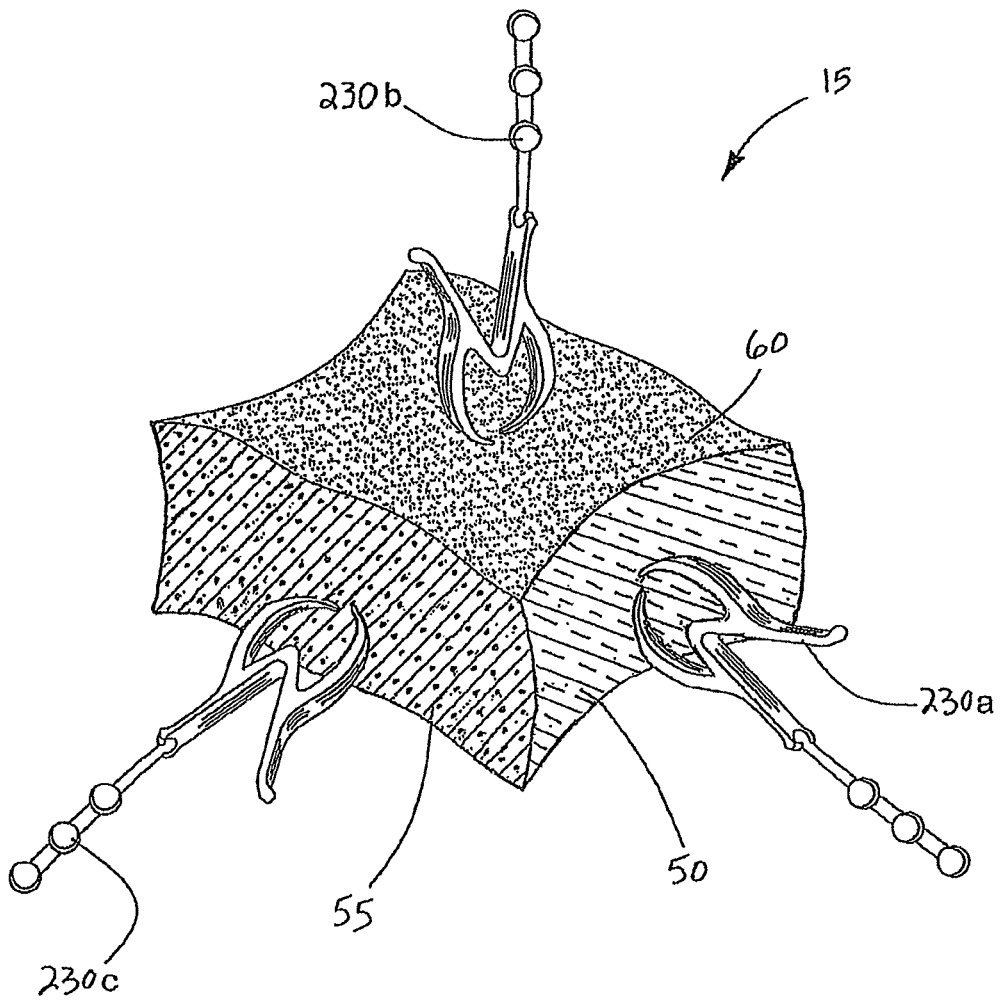
FIG. 11 is an enlarged perspective view of the tissue sample of FIG. 4.

FIG. 11 illustrates an enlarged perspective view of the tissue sample 15 of FIG. 4, which once again has been marked with three different color inks 50, 55, 60 each represented by a different cross hatch pattern. As those of ordinary skill in the art will appreciate, any suitable ink-based system may be utilized including but not limited to those previously described.

Figure 12:
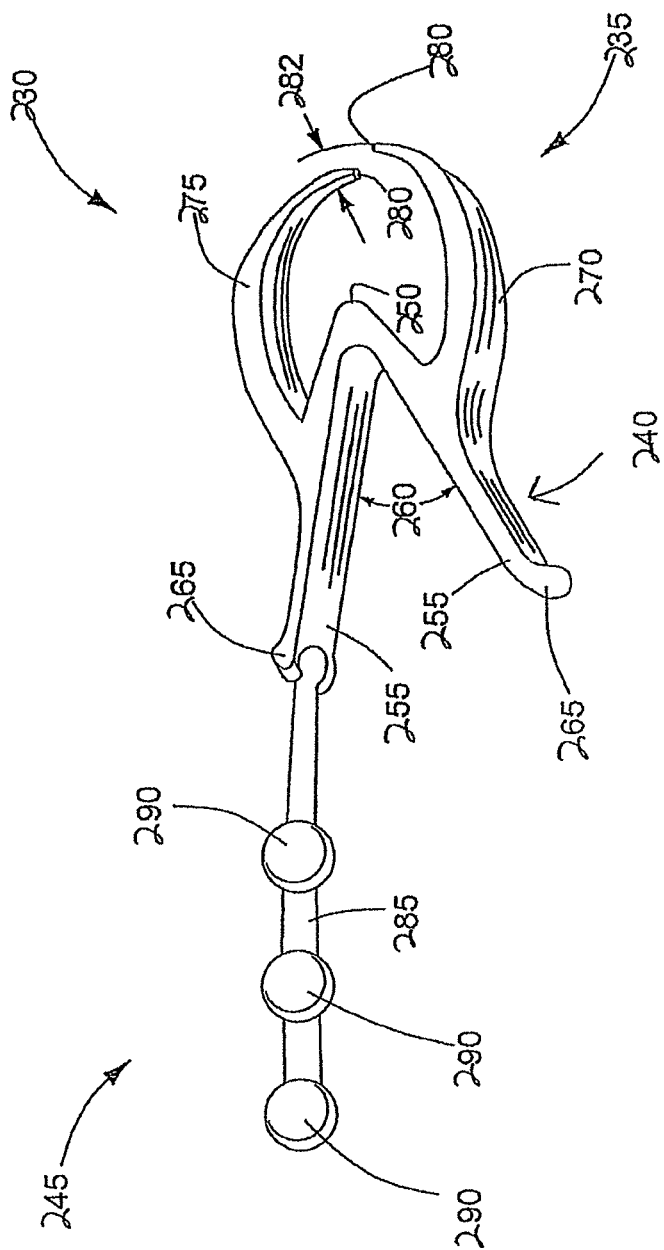
FIG. 12 is a front perspective view of a clip that is attachable to the tissue sample of FIG. 11.
Figure 13:
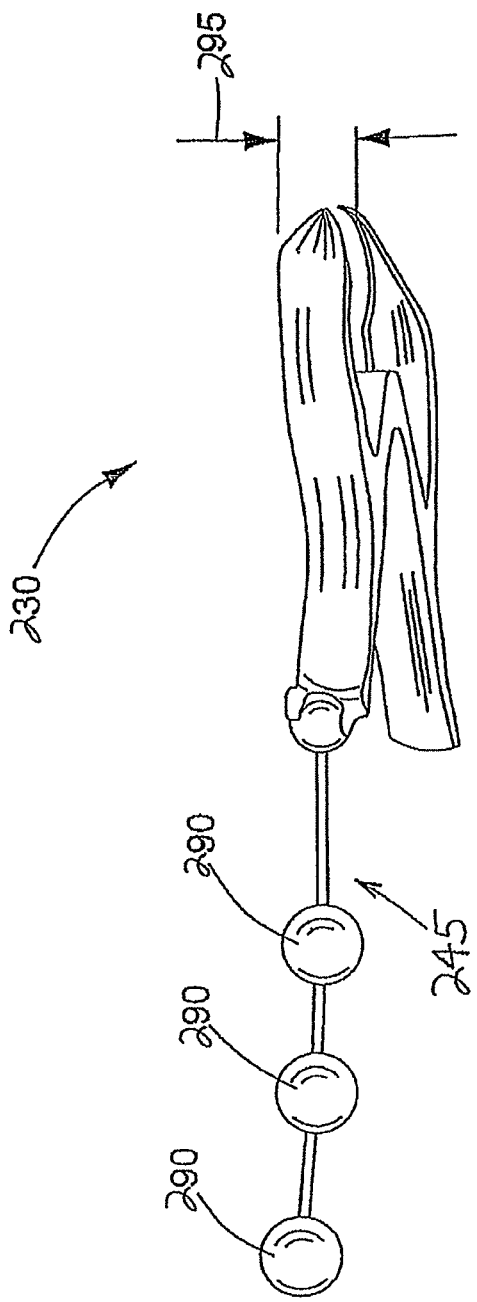
FIG. 13 is top perspective view of the clip of FIG. 12.

FIGS. 12 and 13 illustrate one construction of a clip 230 that may directly engage a tissue sample 15 to identify the orientation of the tissue sample 15 in an X-ray. In preferred constructions, most or all the clip 230 is transparent or translucent in the X-ray region of the electromagnetic spectrum. This allows an X-ray to be taken through the clips 230 such that they do not interfere with the image. The clip 230 includes a jaw portion 235, an actuator portion 240, and a tail 245. The actuator portion 240 is substantially V-shaped and includes an apex 250 and two arms 255 that connect with one another at the apex 250. In the illustrated construction, the two arms 255 cooperate to define an angle 260 of about 45 degrees with other angles 260 also being possible.

In some constructions, the arms 255 include a knob 265 positioned at the end of the arm 255 opposite the apex 250. The knobs 265 make it easier to grasp and actuate the actuator portion 240 without the clip 230 slipping from the user's hand or an instrument. In still other constructions, a texture such as ridges or other grip-enhancing surfaces may be formed on the arms 255 to reduce the likelihood of slippage during actuation.

The jaw portion 235 includes two teeth 270, 275 with each tooth 270, 275 extending from one of the arms 255 of the actuator portion 240. Each tooth 270, 275 is substantially curved and terminates at a point 280. The curve of each of the teeth 270, 275 is such that the two points 280 are pointing substantially toward one another when the clip 230 is in the non-actuated position.

One of the teeth 270 is slightly longer than the other tooth 275 such that the teeth 270, 275 cooperate to produce a slight overbite 282. The overbite 282 improves the grip of the teeth 270, 275 in the tissue sample 15, thereby making it less likely that the clip 230 would be accidentally removed from the sample 15.

In some constructions, barbs or other tissue-engaging members could be formed as part of the teeth 270, 275 to further enhance their grip on the tissue sample 15 to which they are attached. In addition, more than two teeth 270, 275 or teeth 270, 275 having more than one point 280 could also be employed if desired.

Each tooth 270, 275 defines a tooth surface area at the tooth tip. The surface area is related to the biasing force produced by the clip 230. Specifically, the tooth tip surface area is sized to not puncture a glove when only the biasing force of the clip is applied. Thus, when clips with larger biasing forces are employed, larger tooth tip surface areas are employed.

Each tooth 270, 275 attaches to one of the arms 255 of the actuator portion 240 approximately one-third of the length back from the apex 250. The attachment point of the teeth 270, 275 to the arms 255 determines how far open, or apart the points 280 will spread when the clip 230 is in the actuated position. Thus, other constructions could position the teeth 270, 275 further away from the apex 250 and/or could increase the angle 260 defined by the arms 255 to increase the opening between the points 280. Likewise, the opposite arrangement could be employed to reduce the opening if desired.

The tail 245 extends from one of the arms 255 of the actuator portion 240 and includes an indicator 285 that is opaque in an X-ray region of the electromagnetic spectrum. In the illustrated construction, the indicator 285 includes a number of balls 290 formed as part of the tail 245. The balls 290 are substantially opaque in the X-ray region of the electromagnetic spectrum. As such, the balls 290 appear white on an X-ray. In this construction, the number of balls 290 on the tail 245 indicates orientation. For example, as illustrated in FIG. 11, one surface of the sample 15 may have a clip 230a attached with one ball 290 on the tail 245. The second surface would then include a clip 230b with two balls 290, and the third surface would include a clip 230c with three balls 290. Because the clips 230a, 230b, 230c and the tails 245 travel with the sample 15, multiple X-rays at multiple angles can be taken without losing the ability to determine the orientation of the tissue sample 15.

While clips 230 with tails 245 having one, two, or three balls 290 can be provided, one construction employs tails 245 with only three balls 290. The user then breaks off one ball 290 or two balls 290 to define the different indicators 285. Furthermore, while the tail 245 is shown and described as being attached to one of the arms 255, it could be attached to nearly any portion of the actuator portion 240 or the jaw portion 235 if desired.

In other constructions, other indicators 285 may be employed. For example, one construction uses different shaped indicators (e.g., square, rectangular, triangular, etc.) for each clip used to identify orientation (i.e., three clips). Still other constructions may employ indicators that vary by size. For example, one construction could employ a single large ball, a single medium size ball, and a single small ball (or no ball) to indicate orientation.

Figure 14:
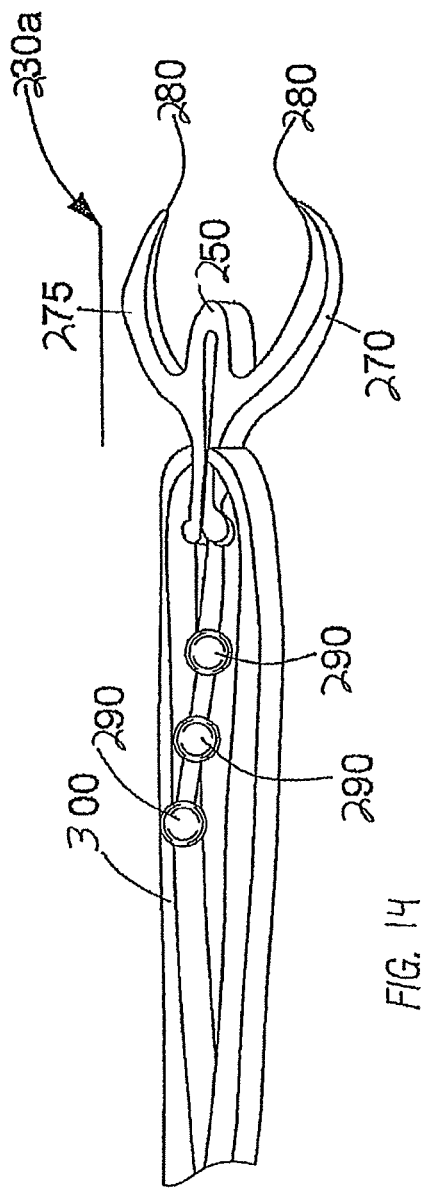
FIG. 14 is a front perspective view of the clip of FIG. 12 in an actuated position.
Figure 15:
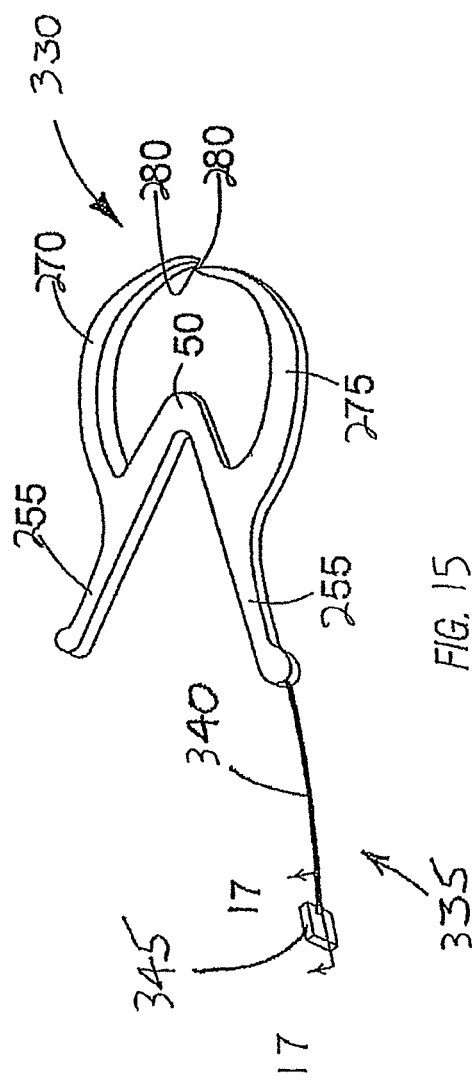
FIG. 15 is a front perspective view of another clip in a non-actuated position.

FIG. 15 illustrates yet another construction of a clip 330 that is suitable for use in identifying the orientation of a tissue sample. The clip 330 is similar to the clips 230a, 230b, 230c of FIGS. 11-14 with the exception of a tail 335. The tail 335 includes an extension portion 340 that connects to one of the arms 255 or some other portion of the clip 330, and an identifier portion 345 that is attached to the extension portion 340.

Figure 16:
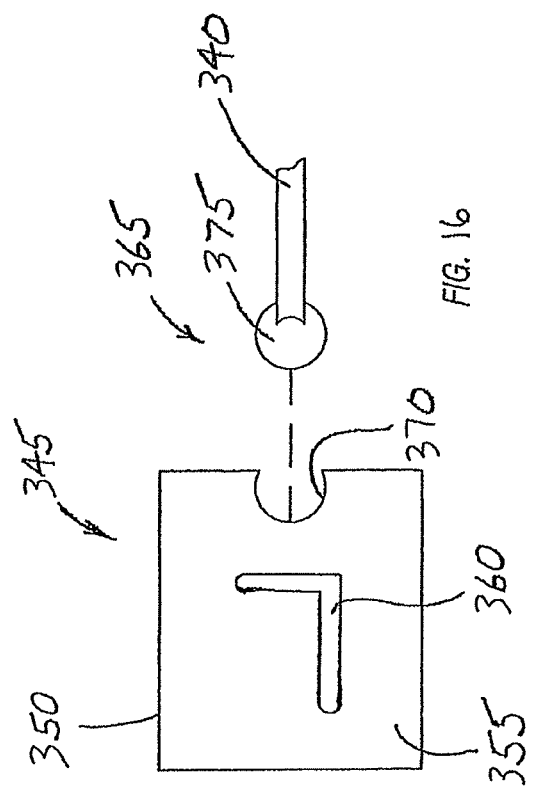
FIG. 16 is an exploded front view of a portion of the clip of FIG. 15.

In the illustrated construction, the extension portion 340 is fixedly attached to the arm 255. In preferred constructions, the extension portion 340 is integrally-formed as part of the arm 255 or clip 330. As illustrated in FIG. 16, the identifier portion 345 includes a substantially plate-shaped member 350. The plate-shaped member 350 defines two relatively large planar surfaces 355 that facilitate the placement of indicia 360 that aids in identifying the orientation of the sample 15 to which the clip 330 is attached. For example, an "L" is placed on one of the planar surfaces 355 to indicate a lateral position. The "L" (Lateral) can be placed on the planar surface 355 using a metallic paint or other system that is visible in an X-ray image. In one exemplary embodiment, the indicia on the planar surface 355 may be applied with a radiographic label. As appreciated by one of ordinary skill in the art, radiographic labels may provide a brightness that is consistent on the X-ray image with edges that are crisp and highly legible. Some other indicia that may be employed includes A for Anterior/Superficial, P for Posterior/Deep, S for Superior/Cephalad, I for Inferior/Caudal, and/or M for Medial. Of course other indicia could be employed so long as the surgeon and the radiologist or pathologist understand their meaning.

Figure 17:
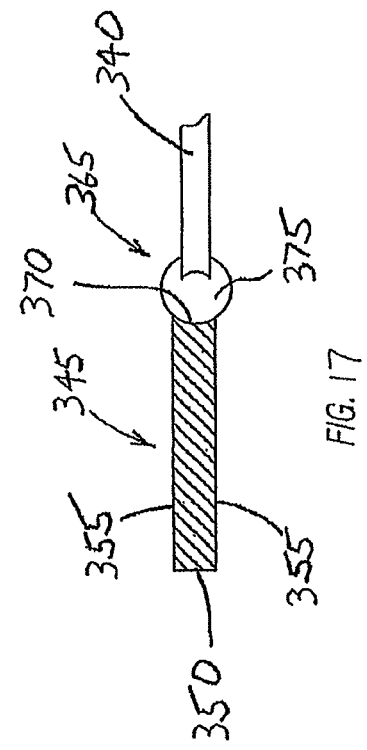
FIG. 17 is a section view of a portion of the clip of FIG. 15 taken along line 17-17 of FIG. 15; and Before any embodiments of the invention are explained, it is to be understood that the invention is not limited in its application to the details of construction and the arrangements of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof is meant to encompass the items listed thereafter and equivalence thereof as well as additional items. The terms "connected," "coupled," and "mounted" and variations thereof are used broadly and encompass direct and indirect connections, couplings, and mountings. In addition, the terms "connected" and "coupled" and variations thereof are not restricted to physical or mechanical connections or couplings.

As illustrated in FIGS. 16 and 17, the identifier portion 345 attaches to the extension portion 340 using a ball-and-socket joint 365. In the illustrated construction, a socket 370 is formed in the identifier portion 345 and a ball 375 is formed at the end of the extension portion 340. The ball 375 fits within the socket 370 and allows movement of the identifier portion 345 with respect to the extension portion 340 and the remainder of the clip 330.

Thus, the clip 330 of FIGS. 15-17 includes an identifier portion 345 that is articulatable with respect to the remainder of the clip 330 to which it is attached. In one construction, the identifier portion 345 is articulatable with respect to the extension portion 340. In another construction, the extension portion 340 is articulatable with respect to the remainder of the clip 330 and the identifier portion 345 is fixed with respect to the extension portion 340. In this construction, the ball-and-socket joint 365, or other joint is formed between the arm 255 and the extension portion 340 similar to the one illustrated in FIG. 12. In still other constructions, both the extension portion 340 and the identifier portion 345 are articulatable with respect to the remainder of the clip 330. These constructions would employ two joints. As one of ordinary skill in the art will recognize, each of these examples describe an arrangement in which the identifier portion 345 is articulatable with respect to the remainder of the clip 330 to allow an X-ray technician to position the identifier portion 345 for optimum viewing in an X-ray image.

One of ordinary skill in the art will realize that many different indicators 285 can be employed so long as they are easily identifiable from any angle on an X-ray image. In addition, while only three clips 230, 330 are required to define an orientation, any number of clips 230, 330 can be employed (e.g., six clips). In addition, a single clip can be employed if desired to identify an area of interest rather than a tissue orientation.

As illustrated in FIG. 13, a width 295 of the clip 230 is small enough to allow the tissue sample 15 and the clip 230 to be compressed during the X-ray process without affecting the connection of the clip 230 and without the clips 230 interfering with the process.

In preferred constructions, the actuator portion 240 and the jaw portion 235 are integrally-formed as a single component. For example, in one construction, the actuator portion 240 and the jaw portion 235 are injection molded as a single part in one manufacturing step. By integrally-molding the actuator portion 240 and the jaw portion 235, the overall cost of the clip 230 is reduced.

In more preferred constructions, the actuator portion 240, the jaw portion 235, and the tail 245 or a portion of the tail 245 are integrally-formed as a single component. In these constructions the actuator portion 240, the jaw portion 235, and the tail 245 can be made from one material in a single injection molding step. Alternatively, two different materials could be used with the actuator portion 240 and the jaw portion 235 being made from a material that is translucent in the X-ray region of the electromagnetic spectrum, and the tail 245 being made from a more opaque material. In these constructions, a co-molding or two step injection molding process may be employed.

With reference again to FIGS. 11, 14, and 15, the use of the clip 230 will be described. Once the tissue sample 15 is removed from the patient, one or more of the surfaces is marked using an ink-based marker as previously described. The actuator portion 240 of the first clip 230a is grasped and compressed to move the clip 230a into the actuated position as shown in FIG. 14. It should be noted that FIG. 14 illustrates an Alice Clamp 300 holding the clip 230a in the actuated position. However, the clip 230a can also be actuated using other surgical instruments (e.g., clamps, forceps, etc.) or a user's fingers. Once in the actuated position, the points 280 of the teeth 270, 275 are positioned adjacent the surface of the tissue sample 15 to be marked and the actuator portion 240 is released. Once released, the teeth 270, 275 move to their non-actuated positions and the points 280 engage the tissue sample 15. These steps are repeated for each additional clip 230b, 230c that is attached to the tissue sample 15. Generally, three clips 230a, 230b, 230c are required to identify the orientation of the sample 15. However more or fewer clips 230 can be employed if desired. Furthermore, the three clips 230a, 230b, 230c may be attached to the same surfaces that were marked with ink, or different surfaces if desired.

When using the clips 330 of FIGS. 15-17, once the clips 330 are attached, an X-ray technician or other user is able to articulate the identifier portions 345 of the various clips 330 to provide optimum viewing in any X-ray images. Thus, the X-ray technician is able to reorient the tissue sample 15 as desired without worrying about losing the orientation and with the knowledge that the identifier portions 345 can be reoriented as required to provide the optimum view of the indicia 360 in any X-ray images.

In one construction, the clips 230a, 230b, 230c are provided with the ink system and are color coded to match the ink colors 50, 55, 60. Thus, the tissue sample 15 is marked with ink 50, 55, 60 and the clips 230a, 230b, 230c are then attached to the surface of the tissue sample 15 corresponding to their particular color.

Once the tissue sample 15 is marked with both ink and the clips 230, both X-ray and visual inspection can be performed without confusing the orientation of the tissue sample 15.

Thus, the invention provides, among other things, a new and useful marking system for use in marking the orientation of a tissue sample 15. The constructions of the clip 230 and the methods of using the clip 230 described above and illustrated in the figures are presented by way of example only and are not intended as a limitation upon the concepts and principles of the invention.

Although the present invention has been described with reference to preferred embodiments, workers skilled in the art will recognize that changes may be made in form and detail without departing from the spirit and scope of the invention.

We claim:

1. A method for marking a tissue sample comprising:
   providing a container including a first ink reservoir containing a first color ink, a second ink reservoir containing a second color ink, and a third ink reservoir containing a third color ink;
   applying the first color ink to a first surface of the tissue sample;
   applying the second color ink to a second surface of the tissue sample;
   applying the third color ink to a third surface of the tissue sample;
   providing first, second, and third tissue marking clips, each of the tissue marking clips including an actuator portion, said actuator portion movable between an actuated position and a non-actuated position;
   a jaw portion coupled to the actuator portion and movable between an open position and a closed position in response to movement of the actuator portion from the non-actuated position to the actuated position, the jaw portion including a first tooth and a second tooth configured to engage the tissue sample when the jaw portion moves from the open position to the closed position;
   a coupling mechanism on one of said actuator portion and said jaw portion; and
   a radiographic indicator configured to be received by said coupling mechanism, and further configured to rotate within said coupling mechanism relative to said one of said actuator portion and said jaw portion during an imaging procedure;
   clipping the first tissue marking clip on the first surface of the tissue sample;
   clipping the second tissue marking clip on the second surface of the tissue sample; and
   clipping the third tissue marking clip on the third surface of the tissue sample.

2. The tissue marking method of claim 1, further comprising removing a cover coupled to the container, the cover fully enclosing the first, second, and third ink reservoirs.

3. The tissue marking method of claim 2, further comprising applying the first color ink to the tissue sample with a first applicator; applying the second color ink to the tissue sample with a second applicator; and applying the third color ink to the tissue sample with a third applicator.

4. The tissue marking method of claim 3, wherein the first, second, and third applicators each include a handle portion and a sponge portion.

5. The tissue marking method of claim 1, further comprising radiographically examining the tissue sample and identifying an orientation of the tissue sample based at least in part on the positions of the first radiographic indicator, the second radiographic indicator, and the third radiographic indicator.

6. A method of marking a tissue sample comprising:
   providing an ink-based applicator device including:
      a container;
      a number of ink reservoirs at least partially defined by the container, each reservoir containing ink of a different color; and
      a cover coupled to and cooperating with the container to fully enclose each of the number of ink reservoirs; and
   providing at least one tissue marking clip including:
      an actuator portion, said actuator portion movable between an actuated position and a non-actuated position;
      a jaw portion coupled to the actuator portion and movable between an open position and a closed position in response to movement of the actuator portion from the non-actuated position to the actuated position, the jaw portion including a first tooth and a second tooth configured to engage the tissue sample when the jaw portion moves from the open position to the closed position;
      a coupling mechanism on one of said actuator portion and said jaw portion; and
      a radiographic indicator configured to be received by said coupling mechanism, and further configured to rotate within said coupling mechanism relative to said one of said actuator portion and said jaw portion during an imaging procedure;
   marking a first surface of the tissue sample with a first color ink.

7. The method of marking a tissue sample according to claim 6 further comprising marking a second surface of the tissue sample with a second color ink.

8. The method of marking a tissue sample according to claim 7 further comprising marking a third surface of the tissue sample with a third color ink.

9. The method of claim 6 further comprising radiographically examining the tissue sample and identifying an orientation of the tissue sample based at least in part on the positions of the first radiographic indicator, the second radiographic indicator, and the third radiographic indicator.

10. The method of claim 8 further comprising identifying an orientation of the tissue sample based at least in part on the first second and third color inks.

11. A method of marking a tissue sample for radiographic examination comprising:
    providing an ink-based applicator device including a number of different colored inks;
    providing at least one tissue marking clip configured to engage the tissue sample the tissue marking clip being transparent to radiographic examination and including a receiving means thereon, said receiving means for receiving a first radiographic indicator that is at least partially opaque to radiographic examination;
    marking at least one surface of said tissue sample with at least one colored ink;
    clipping at least one surface of said tissue sample with said at least one tissue marking clip;
    radiographically examining said tissue sample; and
    identifying the orientation of said tissue sample.

* * * * *